United States Patent [19]

Uy et al.

[11] Patent Number: 5,536,446

[45] Date of Patent: * Jul. 16, 1996

[54] SOLID STATE CONDUCTIVE POLYMER COMPOSITIONS

[75] Inventors: Rosa Uy; Timothy M. Dietz, both of St. Paul, Minn.

[73] Assignee: Minnesota Mining and Manufacturing Company, St. Paul, Minn.

[ * ] Notice: The term of this patent shall not extend beyond the expiration date of Pat. No. 5,338,490.

[21] Appl. No.: 312,698

[22] Filed: Sep. 27, 1994

Related U.S. Application Data

[63] Continuation of Ser. No. 101,812, Jul. 30, 1993, Pat. No. 5,385,679, which is a continuation of Ser. No. 792,957, Nov. 15, 1991, abandoned.

[51] Int. Cl.$^6$ .............................. A61F 13/02; C08J 3/11; C08K 5/11; C08L 5/00

[52] U.S. Cl. ..................... 252/518; 252/500; 525/195; 525/205; 525/57; 524/394; 524/401; 524/516; 524/389; 524/56; 424/448; 526/931

[58] Field of Search ................................. 252/500, 518; 128/640; 607/149, 152, 153; 525/195, 205, 57; 524/394, 401, 516, 389, 56; 424/448; 526/931

[56] References Cited

U.S. PATENT DOCUMENTS

| | | | |
|---|---|---|---|
| 3,998,215 | 12/1976 | Anderson et al. | 128/2.06 |
| 4,273,135 | 6/1981 | Larimore et al. | 128/640 |
| 4,391,278 | 7/1983 | Cahalan et al. | 128/640 |
| 4,406,827 | 9/1983 | Carim | 252/518 |
| 4,524,087 | 6/1985 | Engel | 427/2 |
| 4,539,996 | 9/1985 | Engel | 128/640 |
| 4,554,924 | 11/1985 | Engel | 128/640 |
| 4,593,053 | 6/1986 | Jevne et al. | 523/111 |
| 4,699,146 | 10/1987 | Sieverding | 128/640 |
| 4,715,382 | 12/1987 | Strand | 128/640 |
| 4,750,482 | 6/1988 | Sieverding | 128/156 |
| 4,771,783 | 9/1988 | Roberts | 128/640 |
| 4,795,516 | 1/1989 | Strand | 156/235 |
| 4,798,642 | 1/1989 | Craighead et al. | 156/252 |
| 4,810,418 | 3/1989 | Burvee | 252/500 |
| 4,830,776 | 5/1989 | Thompson | 252/500 |
| 4,846,185 | 7/1989 | Carim | 128/641 |
| 4,848,353 | 7/1989 | Engel | 128/640 |
| 4,855,077 | 8/1989 | Shikinami | 252/518 |
| 4,943,461 | 7/1990 | Karim | 428/40 |
| 4,989,607 | 2/1991 | Keusch et al. | 128/640 |
| 5,003,978 | 4/1991 | Dunsheath, Jr. | 128/640 |
| 5,012,810 | 5/1991 | Strand et al. | 128/640 |
| 5,024,227 | 6/1991 | Schmid | 128/640 |
| 5,223,569 | 6/1993 | Schmid | 524/734 |
| 5,234,992 | 8/1993 | Gyory et al. | 525/57 |
| 5,270,358 | 12/1993 | Asmus | 524/55 |
| 5,276,079 | 1/1994 | Duan et al. | 524/386 |
| 5,338,490 | 8/1994 | Dietz et al. | 252/500 |
| 5,362,420 | 11/1994 | Itoh et al. | 252/500 |

FOREIGN PATENT DOCUMENTS

| | | |
|---|---|---|
| 0058485 | 8/1982 | European Pat. Off. . |
| 0308572 | 3/1989 | European Pat. Off. . |
| 0322098 | 6/1989 | European Pat. Off. . |
| 3917018 | 11/1990 | Germany . |
| 62-292140 | 12/1987 | Japan . |
| 3-162829 | 8/1989 | Japan . |
| WO89/00771 | 1/1989 | WIPO . |
| WO91/09633 | 7/1991 | WIPO . |

OTHER PUBLICATIONS

In Vivo the Business & Medicine Report, *Nov. 1991*, p. 13 (as printed from Fialog information Retreival Service).

Cheradame et al., "Ionically Conducting Polyether Networks", Chapter 5 in MacCallu, Ed. *Polymer Electrolyte Reviews I*, Elsevier Applied Science, New York, 1987.

Errede, "Molecular Interpretations of Sorption in Polymers Part I", *Advanced in Polymer Science*, vol. 99, Springer-Verlag, Berlin Heidelberg Germany (pp. 22–36, 1991).

Gray, "Mixed Polymer Systems", Chapter 6 in MacCallum Ed., *Polymer Electrolyte Reviews I*, Elsevier Applied Science, New York, 1987.

Molyneaux, "Water Soluble Polymers: Properties and Behavior", vol. 1, CRC Press (pp. 151–152) 1983.

Rosiak et al., "Hydrogel Dressings HDR", American Chemical Society Abstract, Aug. 1990 Meeting.

Rosiak et al., "Fast Reaction of Irradiated Polymers—I. Crosslinking and Degradation of Polyvinylpyrrolidone", *Radiat. Phys. and Chem.* vol. 36, 6, pp. 747–755, 1990.

Linke et al., "PVP–A Versatile Specialty Polymer", *Polymer News*, vol. 12, pp. 232–237, 1987.

Spindler et al., "Physical and Spectroscopic Properties of Ternary Polymr Electrolytes Composed of Poly(vinylpyrrolidone), Poly(ethylene glycol), and Lithium Trifluoromethanesulfonate", *Macromolecules*, 1986, 19, 347–350.

Hardy et al., "Preparation and Electrical Response of Solid Polymer Electrolyte with Only One Mobile Species", *J. Am. Chem. Soc.*, 1985, 107, 1984.

Hardy et al., "Chloride Ion Conductivity in a Plasticized Quaternary Ammonium Polymer", *Macromolecules*, 17, 1984, 975–977.

*Primary Examiner*—Douglas J. McGinty
*Attorney, Agent, or Firm*—Gary L. Griswold; Walter N. Kirn; John H. Hornickel

[57] ABSTRACT

Solid state conductive polymer compositions which are ionically-conductive regardless of the amount of water present in the composition are disclosed. The compositions have solvating polymer, ionic salt, and optionally if the composition is not cohesive and pliable, essentially non-volatile plasticizer in an amount sufficient to render the composition cohesive and pliable. Biomedical electrodes having means for electrical communication contacting the compositions are also disclosed. Methods of making the compositions and electrodes are also disclosed.

7 Claims, 1 Drawing Sheet

SOLID STATE CONDUCTIVE POLYMER COMPOSITIONS

This is a continuation of application Ser. No. 08/101,812 filed Jul. 30, 1993 now U.S. Pat. No. 5,385,679, which is a continuation of Ser. No. 07/792,597 filed Nov. 15, 1991, abandoned.

FIELD OF THE INVENTION

This invention relates to solid state conductive polymer compositions which are ionically-conductive regardless of the amount of water present in the composition, biomedical electrodes containing such compositions, and a method of preparing such compositions.

BACKGROUND OF THE INVENTION

Modern medicine uses many diagnostic, therapeutic, and electrosurgical procedures where electrical signals or currents are received from or delivered to a patient's body. The interface between medical equipment used in these procedures and the skin of the patient is usually some sort of biomedical electrode. Such an electrode typically includes a conductor which must be connected electrically to the equipment, and a conductive medium adhered to or otherwise contacting skin of a patient.

Among the therapeutic procedures using biomedical electrodes are transcutaneous electronic nerve stimulation (TENS) devices used for pain management; neuromuscular stimulation (NMS) used for treating conditions such as scoliosis; defibrillation electrodes to dispense electrical energy to a chest cavity of a mammalian patient to defibrillate heart beats of the patient; and dispersive electrodes to receive electrical energy dispensed into an incision made during electro surgery.

Among diagnostic procedures using biomedical electrodes are monitors of electrical output from body functions, such as electrocardiogram (ECG) for monitoring heart activity and for diagnosing heart abnormalities.

For each diagnostic, therapeutic, or electrosurgical procedure, at least one biomedical electrode having an ionically-conductive medium containing an electrolyte is adhered to or otherwise contacting mammalian skin at a location of interest and also electrically connected to electrical diagnostic, therapeutic, or electrosurgical equipment. A critical component of the biomedical electrode is the conductive medium serving as the interface between mammalian skin and diagnostic, therapeutic, or electrosurgical equipment.

The conductive medium conventionally employed in biomedical electrodes utilizes one of two classes of polymer conductive materials: gel electrolytes or polyelectrolytes. Both gel electrolytes and polyelectrolytes are ionically-conductive polymer systems in the form of conductive gels, creams, and conductive adhesives.

As discussed in Chapter 6, "Mixed Polymer Systems" by F. M. Gray in MacCallum, Ed., *Polymer Electrolyte Reviews I*, Elsevier Applied Science, New York (1987), at pages 139–141 gel electrolytes have been defined as polymer-solvent-salt systems which the role of the polymer is secondary in the conducting matrix. The polymer serves as a thickener for low molecular weight, high dielectric constant solvents which solvate the salt and act as the conducting medium.

The solvent can be either an aqueous solution or a co-solvent consisting of water and a polyhydric alcohol. U.S. Pat. No. 4,406,827 (Carim) describes the utilization of gel electrolyte in biomedical electrodes, in which a guar gum network serves as a matrix to confine a solution of potassium chloride. To function properly, the conductive guar gum gel electrolyte system requires the presence of water. Unfortunately, gel electrolyte systems are susceptible to dehydration of the essential water needed to maintain ionic conductivity.

Also as discussed by Gray at pages 139–141, a polyelectrolyte is a conductive matrix formed by the dissolution of an ionic polymer in an aqueous medium. Ionic polymers are hybrids of ionic salts and covalent polymers, and can have structural features common to both.

Again, water is a necessary component to the polymer system, in order to dissociate ions of the ionic polymer and to plasticize the polymer to increase ionic mobility. Ionic conductivity of a polyelectrolyte is a function of the amount of water content. U.S. Pat. No. 4,524,087 (Engel) describes a biomedical electrode employing a polyelectrolyte polymer conductive material. In this instance, the polyelectrolyte is a conductive adhesive consisting of a partially neutralized polyacrylic acid homopolymer dispersed in water and glycerin. Unfortunately, polyelectrolyte-containing biomedical electrodes are also susceptible to dehydration of water which reduces ionic conductivity of the polymer.

The loss of water from biomedical electrodes using either gel electrolytes or polyelectrolytes has been an unresolved problem. Despite efforts to provide packaging which stabilizes the water vapor pressure of a biomedical electrode within a package, once a biomedical electrode is exposed to the general atmosphere, dehydration commences, resulting in unacceptable electrical properties. In the case of polyelectrolytes, having adhesive properties, dehydration also results in decreasing adhesion of the electrode to mammalian skin.

An approach to making a dry polyelectrolyte biomedical electrode is disclosed in U.S. Pat. No. 5,003,978 (Dunsheath, Jr.) where a conductive adhesive is coated on a conductive substrate. The substrate is composed of polymer materials having finely ground powders loaded therein. The conductive adhesive is composed of a water-based adhesive having a diffusion of chloride ions throughout the adhesive. Water in the adhesive is less than 5% by weight.

Another approach to making a dry polyelectrolyte biomedical electrode is disclosed in U.S. Pat. No. 4,273,135 (Larimore et al.). The conductive material consists essentially of a cohesive, conformable, nonionic hydrophilic synthetic polymer including non-ionic water-soluble polymers of substantially all water soluble monomers which is plasticized with agents compatible with the polymer. At the time of application of an electrode, skin of a patient is lightly abraded and dampened with water or normal saline solution to provide electrolytic conductivity. Thus, water or an aqueous solution is required for use even if the electrode is dry during storage.

A third class of polymer conductive materials is known and the subject of MacCallum, Ed., Polymer Electrolyte Reviews I, described above, and specifically Chapters 5 and 6 by Gray therein. These materials are called polymer electrolytes, which are ionically-conductive polymer materials where ionic salts are dissolved directly into a solvating polymer matrix. Therefore, direct interaction between non-carbon atoms in the polymer backbone of the polymer and the cation of the salt yields a conductive solid solution.

One conductive polymer electrolyte having high ionic conduction is disclosed in U.S. Pat. No. 4,855,077 (Shikinami et al.). In this instance, the polymeric ionic conductor is composed of segmented polyurethane having polyethylene oxide, polypropylene oxide, etc. in the segments thereof and having a high ionic conduction by a complex formed by the segment and an ionic compound. The use of a polyalkylene oxide achieves a polymer which has an amorphous phase aggregate almost all or completely all of which is in the rubbery state because the glass transition temperature of the polyalkylene oxide is lower than room temperature. Thus, the polymer can become a material with sticking property and can include a plasticizer added thereto for imparting tack. However, Shikanami et al. require the polymerization of a polyurethane from prepolymers using organic solvent systems, which could leave residual oligomeric units in the final product.

SUMMARY OF THE INVENTION

The present invention achieves a solid state conductive polymer composition which is ionically-conductive regardless of the amount of water present during manufacture, storage or use. Solid state conductive polymer compositions of the present invention are not susceptible to a loss of conductivity due to dehydration of water or other volatile components after manufacture and prior to completion of use. Nor is the conductivity of such compositions impaired by the absorption of water into such compositions in humid atmospheric conditions.

Compositions of the present invention can be made with minimal amounts of water present during manufacture. Such compositions can be stored in humid or arid conditions without protection from atmospheric moisture. Such compositions can be used without regard to the amount of atmospheric moisture or body fluids or exudate likely to be encountered during diagnostic, therapeutic, or electrosurgical procedures. In short, compositions of the present invention solve the problem of requiring water to achieve ionical conductivity in compositions in biomedical electrodes which contact mammalian skin. Compositions of the present invention function independently of the presence or absence of water. Water is accommodated in such compositions, but not required for use.

Solid state conductive polymer compositions of the present invention can be used as the conductive medium in a biomedical electrode conductively interfacing between mammalian skin and means for electrical communication to electrical diagnostic, therapeutic, or electrosurgical equipment.

A solid state conductive polymer composition ionically-conductive regardless of an amount of water present in the composition comprises a polymer electrolyte complex and optionally if the complex is not cohesive and pliable, an essentially non-volatile plasticizer in an amount sufficient to render the composition cohesive and pliable. A polymer electrolyte complex comprises a solid solution of ionic salt dissolved in a solvating polymer. A conductive solid solution is achieved through dissociation of ionic salts by a solvating polymer, forming a cation-polymer complex and its counterion. The cation-polymer complex occurs with direct interaction of non-carbon atoms in the polymer chain.

A solvating polymer can be either a homopolymer where each monomeric unit has at least one ionizing non-carbon atom or a copolymer where at least one monomeric unit has at least one ionizing non-carbon atom contained in a pendant group to the monomeric unit.

The invention also achieves the use of a solid state conductive polymer composition described above as a conductive medium in a biomedical electrode.

A biomedical electrode comprises a conductive medium, a solid state conductive polymer composition described above and means for electrical communication interacting between the conductive medium and electrical diagnostic, therapeutic, or electrosurgical equipment.

It is a feature of the present invention that no water or other volatile plasticizer is required to insure ionic conductivity in a solid state conductive polymer composition of the present invention.

It is another feature of the invention that solid state conductive polymer compositions of the present invention can use plasticizers which are essentially non-volatile at ambient conditions.

It is another feature of the present invention that biomedical electrodes containing solid state conductive polymer compositions of the present invention are not susceptible or otherwise sensitive to dehydration or evaporation of other volatile liquid.

It is another feature of the present invention that biomedical electrodes containing solid state conductive polymer compositions of the present invention can be stored in open containers to the atmosphere, requiring fewer packaging limitations than presently required for biomedical electrodes requiring the presence of water for ionic conductivity.

It is an advantage of the invention that solid state conductive polymer compositions of the present invention can be plasticized to provide a broad scope of conductive materials, ranging from non-volatile gels and creams to non-volatile conductive adhesives.

It is another advantage of the present invention that more consistent impedance can be achieved during use in diagnostic procedures because biomedical electrodes containing solid state conductive polymer compositions of the present invention function regardless of the amount of water or polar solvent present in the composition.

It is another advantage of the present invention that use of biomedical electrodes having compositions of the present invention do not require special skin preparations prior to use. Indeed the absence of water reduces the incidence of a "cold" feeling when a biomedical electrode of the present invention contacts mammalian skin.

It is another advantage of the present invention that compositions of the present invention can provide ionic conductivity as an extremely thin coating on a means for electrical communication for a biomedical electrode. Thus, biomedical electrodes of the present invention can have a low profile and can be conformable to a variety of contours on mammalian skin. Another aspect of the present invention is the ease by which solid state conductive polymer compositions of the present invention can be made. A method of preparing a non-volatile, solid state conductive polymer composition comprises mixing a solvating polymer, an ionic salt, and an essentially non-volatile plasticizer, if any is needed to render the composition cohesive and pliable, into an essentially volatile solvent and removing solvent to form a non-volatile solid state conductive polymer composition regardless of an amount of water present in the composition.

Evaporation is a preferred method of reducing the amount of essentially volatile solvent for manufacturing efficiency. The extent of evaporating can be adjusted according to preferences of one skilled in the art. Because solid state conductive polymer compositions of the present invention maintain conductivity regardless of the amount of water present in the composition, it is preferred to nearly completely evaporate such volatile solvent when making compositions of the present invention.

It is a feature of that aspect of the present invention that a method of preparing solid state conductive polymer compositions of the present invention do not require, but can accommodate the continued presence of essentially volatile liquids in the composition.

It is another feature of the present invention that a solid state conductive polymer composition can be made in an extremely thin coating of less than about 0.25 mm on a substrate, preferably a substrate with an electrically conductive surface.

It is another feature of the present invention that a solid state conductive polymer composition can be made using a volatile solvent such as water which is environmentally preferred.

It is an advantage of the present invention that a method of preparing solid state conductive polymer compositions of the present invention can be achieved with a minimum number of steps employing ecologically compatible materials.

EMBODIMENTS OF THE INVENTION

Solvating Polymer

Figure 1:
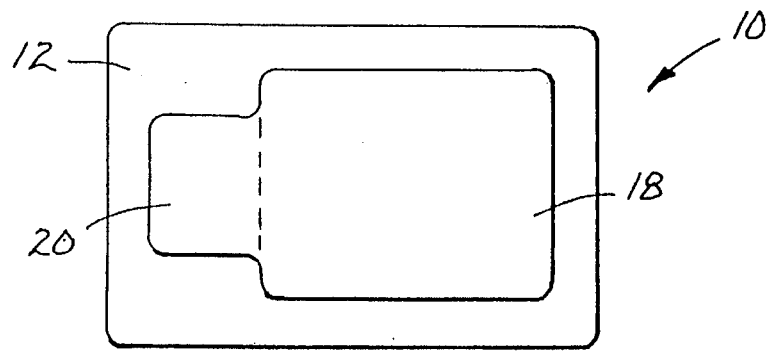
FIG. 1 is a top plan view of a biomedical electrode containing a solid state conductive polymer composition of the present invention.

Solvating polymers useful in solid state conductive polymer compositions of the present invention can be either a homopolymer where each monomeric unit has at least one ionizing non-carbon atom or a copolymer where at least one monomeric unit has at least one ionizing non-carbon atom contained in a pendant group to the monomeric unit. Nonlimiting examples of a non-carbon atom in a monomeric unit include oxygen, nitrogen, sulphur, and phosphorus.

Of possible solvating polymers, poly(N-vinyl lactam); polyacrylamide or its ionic forms; polyacrylic acid or its salts; poly(vinyl alcohol) prepared from hydrolyzing polyvinyl acetate; poly(vinyl methyl ether); poly(2-acrylamido-2-methylpropanesulfonic acid), its salts, copolymers of the acid, copolymers of salts of the acid, or mixtures thereof; or combinations of these solvating polymers are useful. Of these possible solvating polymers, crosslinked poly(N-vinyl lactam); crosslinked polyacrylamide; crosslinked polyacrylic acid or its salts; crosslinked poly(acrylamido-2-methylpropanesulfonic acid), its salts, crosslinked copolymers of the acid, crosslinked copolymers of salts of the acid or mixtures thereof; or combination of these crosslinked solvating polymers are preferred. Of these preferred solvating polymers, a crosslinked poly(N-vinyl lactam) is especially preferred.

Solvating polymer can be present in a conductive polymer composition in an amount from about 5 to 98 weight percent. In a composition in which a plasticizer is added to render the composition cohesive and pliable, the solvating polymer can comprise from about 5 to about 50 weight percent, and preferably from about 20 to about 45 weight percent, of the conductive polymer composition.

Poly(N-vinyl lactam) can be a noncrosslinked homopolymer or a noncrosslinked copolymer containing N-vinyl lactam monomeric units, which after crosslinking, such as by irradiation, is swellable in a plasticizer biocompatible with mammalian skin.

Preferably, noncrosslinked homopolymer or noncrosslinked copolymer is soluble in plasticizer biocompatible with mammalian skin in the absence radiation crosslinking. N-vinyl lactam monomeric units comprise a majority of total monomeric units of the polymer.

Nonlimiting examples of N-vinyl lactam monomers are N-vinyl-2-pyrrolidone; N-vinyl-2-valerolactam; N-vinyl-2-caprolactam; and mixtures of any of the foregoing. Preferably, the N-vinyl lactam is N-vinyl-2-pyrrolidone. Preferably, the poly(N-vinyl lactam) is a homopolymer of N-vinyl-2-pyrrolidone.

Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

The N-vinyl lactam monomeric units comprise no less than about 50 weight percent of the monomeric units present in the poly(N-vinyl lactam) in solid state form. More preferably, the N-vinyl lactam monomeric units comprise 70 to 100 percent by weight of the poly(N-vinyl lactam) and most preferably 90 to 100 percent by weight of the poly(N-vinyl lactam).

Noncrosslinked poly(N-vinyl lactam) homopolymer and poly(N-vinyl pyrrolidone)/poly vinyl acetate copolymers are commercially available. Nonlimiting examples of commercially available poly(N-vinyl pyrrolidone) useful for the present invention include Aldrich Chemical Co. of Wilwaukee, Wis., BASF of Parsippany, N.J., and GAF of Wayne, N.J.

Poly(N-vinyl lactam) can have a Fikentscher K-value of at least K-15 and preferably at least K-60, and most preferably at least K-90. Fikentscher K-values are described in Molyneaux, Water-Soluble Polymers: Properties and Behavior, Vol. 1, CRC Press, 1983, pp. 151–152.

After exposure to ionizing radiation, poly(N-vinyl lactam) can have a Swelling Capacity, S, milliliters of liquid sorbed per gram of polymer, of at least about 15 in water, preferably about 20–35 in water, and most preferably about 25 in water.

Swelling Capacity correlates to a measurement of polymer swelling as a function of chemical crosslinking units in poly(N-vinyl lactam), according to the equation:

$$S = C(\lambda^{1/3} - \lambda_o^{1/3})$$

where S is a measurement of water sorbed per gram of polymer, C is a constant characteristic of the polymer, i.e., milliliters of water sorbed per gram of polymer, $\lambda$ is the average number of backbone atoms in the polymer segments between crosslinked junctions, and $\lambda_o$ is the average number of backbone carbon atoms in the polymer segments between crosslinked junctions when S is zero. Swelling capacity and this equation are discussed in Errede, "Molecular Interpretations of Sorption in Polymers Part I" *Advances in Polymer Science* Vol. 99, Springer-Verlag, Berlin Heidelberg Germany (pp. 21–36, 1991), the disclosure of which is incorporated by reference.

Poly(N-vinyl lactam) useful in the present invention can be in any form susceptible to being crosslinked, but preferably is in a solid state form. Nonlimiting examples of solid state forms include particles, pellets, sheets, strands, fibers, membranes, films, and other three dimensional functional forms. Preferably, poly(N-vinyl lactam) is in the form of particles of a size from about 0.1 micrometers to about 250 micrometers and preferably from about 10 micrometers to about 75 micrometers.

Crosslinked poly(N-vinyl lactam) compositions can be prepared using free-radical polymerization methods employing chemical crosslinking agents such as that disclosed in U.S. Pat. No. 4,848,353 (Engel) or EPO Publication 0 322 098 (Duan) or using ionizing radiation such as that disclosed in U.S. Pat. No. 5,276,079 (Duan et al.), the disclosures of such methods of crosslinking being incorporated by reference as if rewritten herein.

Crosslinked polyacrylamide; crosslinked polyacrylic acid or its salts; crosslinked poly(2 -acrylamide-2-methylpropanesulfonic acid or its salts, crosslinked copolymers of the acid, crosslinked copolymers of salts of the acid or mixtures thereof; or combinations thereof can be prepared by using free-radical polymerization methods known to those skilled in the art.

Essentially Non-volatile Plasticizer

If solid state conductive polymer compositions require a plasticizer to render the composition cohesive and pliable, and preferably pressure sensitive adhesive, the plasticizer can be an essentially non-volatile liquid or combination of liquids which can swell the solvating polymer and which is biocompatible with mammalian skin.

Essentially non-volatile means that a plasticizer as used in the present invention will render a polymer electrolyte complex of solvating polymer and ionic salt sufficiently cohesive and pliable such that less than ten percent (10%) of a given volume of plasticizer evaporates after exposure to a temperature of processing the composition or to a temperature of storage conditions.

Non-limiting examples of essentially non-volatile plasticizers include polyhydric alcohols (e.g., ethylene glycol, propylene glycol, sorbitol, polyethylene glycol, and glycerin) and other plasticizers which are non-volatile in ambient conditions and do not cause mammalian skin irritation or toxic reaction.

Essentially non-volatile plasticizer can be added in an amount sufficient to render a solid state conductive polymer composition cohesive and pliable, and preferably also pressure-sensitive adhesive. The amount of plasticizer to be added to form a cohesive, pliable, solid state conductive pressure-sensitive adhesive depends on the type of solvating polymer employed and the extent of crosslinking in the solvating polymer.

The essentially non-volatile plasticizer can be added to solvating polymer ranging from about 0 to about 95 weight percent of the solid state conductive polymer composition. One can adjust the amount of plasticizer employed to control adhesive properties of the polymer electrolyte complex. Preferably, the amount of plasticizer added can range from about 50 to 75 weight percent of the composition when the solvating polymer is crosslinked poly(N-vinyl lactam). Preferably, the amount of plasticizer can range from about 65 to 75 weight percent of the composition when the solvating polymer is crosslinked polyacrylic acid; crosslinked polyacrylamide; or crosslinked poly(2-acrylamido- 2-methylpropanesulfonic acid) or its salts, crosslinked copolymers of the acid, crosslinked copolymers of salts of the acid, or mixtures thereof.

Of essentially non-volatile plasticizers, glycerin and polyethylene glycol are preferred, with polyethylene glycol most preferred. Glycerin and polyethylene glycol can be used in mixtures. Glycerin can comprise up to 100 weight percent of the essentially non-volatile plasticizer. Preferably, polyethylene glycol can comprise up to 100 weight percent of the essentially non-volatile plasticizer. Polyethylene glycol of either 300 molecular weight or 400 molecular weight is preferred, with 300 molecular weight more preferred.

Unexpectedly, solid state conductive polymer compositions of the present invention do not require the use of water, or the retention of water or any other volatile liquid capable of vaporization at ambient conditions, as a plasticizer for polymer electrolyte complex used in the present invention to provide ionic conductivity. By relying on essentially non-volatile plasticizers to render solid state conductive polymer compositions cohesive and pliable, and preferably pressure-sensitive adhesive, biomedical electrodes employing such solid state conductive polymer compositions are less apt to have ionic conductivity altered by dehydration of a component of the composition.

While solid state conductive polymer compositions of the present invention do not require water to be present, such compositions can accommodate the presence of water in such composition without losing ionic conductivity or adhesive performance. Thus, solid state conductive polymer compositions of the present invention function regardless of the amount of water present during manufacture, storage, or use.

Ionic Salts

Solvating polymers contain one or more ionic salts in amounts sufficient to interact with non-carbon atoms of the solvating polymer in order to form polymer electrolyte complexes which can be plasticized to form solid state conductive polymer compositions of the present invention. In effect, solid state conductive polymer composition is a matrix of (a) a conductive solid solution of one or more ionic salts dissociating in a solvating polymer and (b) an essentially non-volatile plasticizer present, if any, in an amount sufficient to render the matrix cohesive and pliable, and preferably pressure-sensitive adhesive. Thus, unexpectedly, the interaction of ionic salts with the solvating polymer provides ionic conductivity for the composition. Ionic or polar solvents such as water previously employed in polyelectrolyte compositions are not necessary to provide ionic conductivity in a conductive medium of a biomedical electrode.

Non-limiting examples of ionic salts useful for interaction with the solvating polymer include lithium chloride, lithium perchlorate, sodium citrate, and preferably potassium chloride.

To provide acceptable ionic conductivity, ionic salts can be present in amounts from about 0.5 weight percent to about 5 weight percent of the solid state conductive polymer composition. Preferably, ionic salts are present in amounts from about 2 to about 3 weight percent of the solid state conductive polymer composition.

Biomedical Electrodes

Biomedical electrodes employing solid state conductive polymer compositions of the present invention are useful for diagnostic, therapeutic and electrosurgical purposes. In its most basic form, a biomedical electrode comprises a conductive medium contacting mammalian skin and a means for electrical communication interacting between the conductive medium and electrical diagnostic, therapeutic, or electrosurgical equipment.

Figure 2:
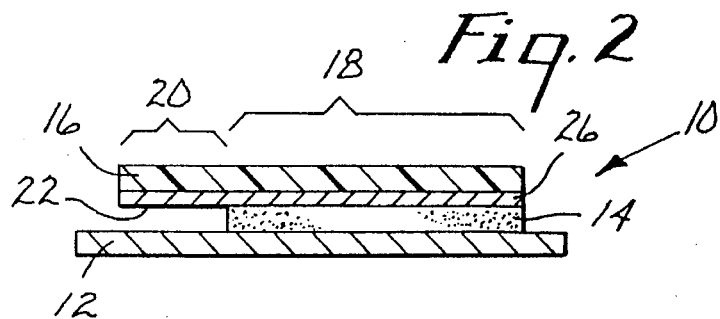
FIG. 2 is a sectional view of the biomedical electrode of FIG. 1.

FIGS. 1 and 2 show either a disposable diagnostic electrocardiogram (EKG) or a transcutaneous electrical nerve stimulation (TENS) electrode 10 on a release liner 12. Electrode 10 includes a field 14 of a biocompatible and adhesive conductive medium for contacting mammalian skin of a patient upon removal of protective release liner 12. Electrode 10 includes means for electrical communication 16 comprising a conductor member having a conductive interface portion 18 contacting field 14 of conductive medium and a tab portion 20 not contacting field 14 of conductive medium for mechanical and electrical contact with electrical instrumentation (not shown). Means 16 for electrical communication includes a conductive layer 26 coated on at least the side 22 contacting field 14 of conductive medium.

It is foreseen that a typical EKG conductor member 16 will comprise a strip of material having a thickness of about 0.05–0.2 millimeters, such as polyester film and have a coating 26 on side 22 of silver/silver chloride of about 2.5–12 micrometers, and preferably about 5 micrometers thick thereon. Presently preferred is a polyester film commercially available as "Mellinex" 505-300, 329, 339 film from ICI Americas of Hopewell, Va. coated with a silver/silver chloride ink commercially available as "R-300" ink from Ercon, Inc. of Waltham, Mass. A TENS conductor member 16 can be made of a non-woven web, such as a web of polyester/cellulose fibers commercially available as "Manniweb" web from Lydall, Inc. of Troy, N.Y. and have a carbon ink layer 26 commercially available as "SS24363" ink from Acheson Colloids Company of Port Huron, Mich. on side 22 thereof. To enhance mechanical contact between an electrode clip (not shown) and conductor member 16, an adhesively-backed polyethylene tape can be applied to tab portion 20 on the side opposite side 22 having the conductive coating 26. A surgical tape commercially available from 3M Company as "Blenderm" tape can be employed for this purpose.

Another type of therapeutic procedure, which can employ a biomedical electrode having a solid state conductive polymer composition of the present invention, is the dispensing of electrical energy to the chest cavity of a mammalian patient to defibrillate abnormal heart beats of the patient. Delivery of a high (e.g., 2000 volts) voltage, high (e.g., 40 amps) current electrical charge through one biomedical electrode and receipt of that electrical charge through another biomedical electrode completes the electrical circuit. An example of an electrode useful for defibrillation is disclosed in U.S. Pat. No. 3,998,215 (Anderson et al.), which is incorporated herein by reference.

Another type of therapeutic procedure involving application of electrical current to skin of a patient is iontophoresis, which delivers an iontophoretically active pharmaceutical to or through mammalian skin with aid of an electrical current.

Another type of medical procedure employing a biomedical electrode using a solid state conductive polymer composition of the present invention is electrosurgery. In this instance, the biomedical electrode serves to receive in a dispersed fashion electrical signals introduced to the patient at an incision site using an electro-surgical cutting electrode. An electro-surgical system usually comprises a generator providing high-frequency alternating current on demand under monitored conditions, the cutting electrode having an extremely high-current density and a flat dispersive biomedical electrode having a very large surface area to provide a low-current density. The dispersive biomedical electrode is placed in intimate and continuous contact with a portion of the mammalian skin which is not subject to the surgical procedure. The alternating current circuit is completed through the body of the patient between the dispersive biomedical electrode and the cutting electrode. Disconnection of the dispersive electrode either from contacting the patient or from the generator could subject the patient to electrical burns where the alternating current circuit leaves the body of the patient.

Figure 3:
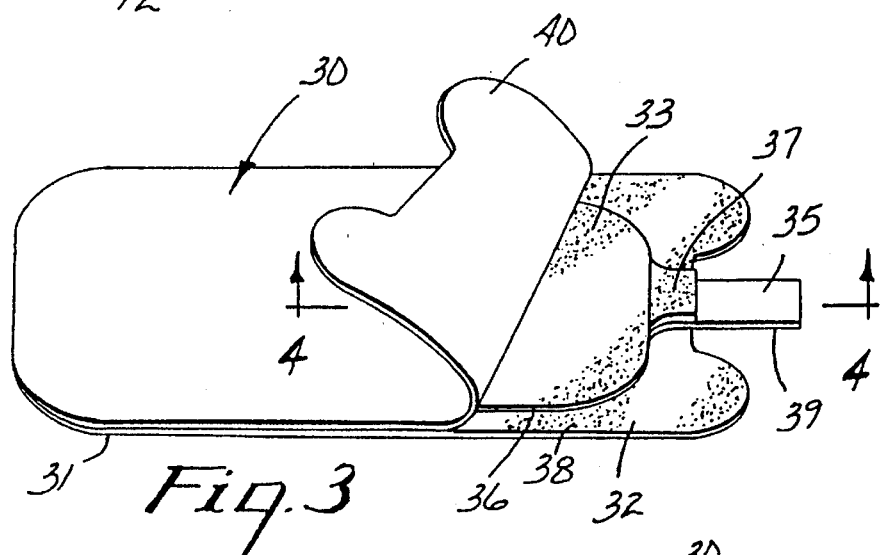
FIG. 3 is a perspective view of a dispersive biomedical electrode used for receiving electrical current during electrosurgery.
Figure 4:
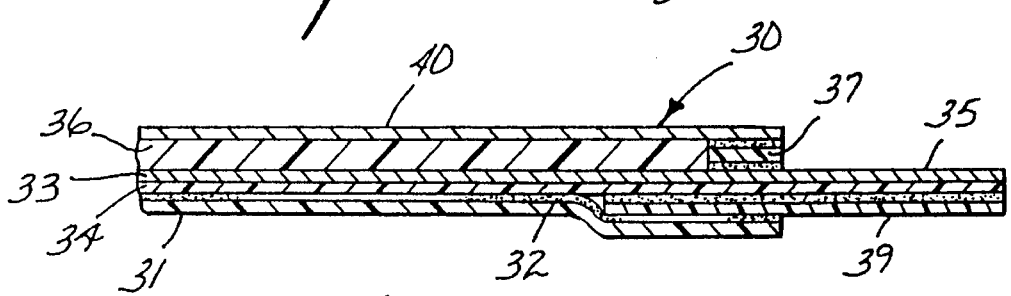
FIG. 4 is a cross-sectional view of the dispersive biomedical electrode of FIG. 3.

A dispersive electrode is seen in FIGS. 3 and 4. Dispersive electrode 30 comprises an insulating backing 31 coated on one surface with a biocompatible pressure sensitive adhesive 32. The backing 31 can be a closed cell polyethylene foam. An electrode plate 33 adheres to a portion of the biocompatible pressure sensitive adhesive 32. The electrode plate 33 can be an aluminum foil or a conformable polymeric backing 34, e.g., polyester, having aluminum deposited on one surface. The electrode plate 33 has an integrally associated connector tab 35 suited to electrically connect the dispersive electrode 30 to a leadwire which in use is connected to an electrosurgery generator. A field of electrically-conductive adhesive 36 of the present invention coats the entire electrically-conductive surface of electrode plate 33 except the connector tab 35. An insulating strip 37 double coated with pressure sensitive adhesive covers that portion of the surface of the connecting tab 35 which underlies the backing 31 and biocompatible pressure sensitive adhesive 32. The backing 31 and biocompatible pressure sensitive adhesive 32 have an apron 38 extending beyond the periphery of the electrode plate 33 and electrically-conductive adhesive 36. Apron 38 and insulating strip 37 serve to insulate the electrode plate 33 from direct contact with a patient's skin, thereby avoiding thermal burns, and from contact with other conductors (e.g., blood or water) which may result in an electrical short circuit. Supporting connecting tab 35 is a reinforcing layer 39 of nonwoven polyester contating adhesive 32 and having a single coated adhesive layer contacting tab 35. An optional release liner 40 can be used to protect adhesives 32 and 36 prior to use.

Preferably, to achieve excellent adhesion and electrical contact with a patient's skin (avoiding hot spots or loss of contract due to motion), surface area of plate 33 and adhesive 36 of the present invention are about 130 $cm^2$. Preferably, the adhesive 36 of the present invention is coated about 0.5 mm thick. Other examples of biomedical electrodes which can use solid state conductive polymer compositions of the present invention as conductive adhesive fields include electrodes disclosed in U.S. Pat. Nos. 4,527,087; 4,539,996; 4,554,924; 4,848,353 (all Engel); 4,846,185 (Carim); 4,771,713 (Roberts); 4,715,382 (Strand); 5,012,810 (Strand et al.); co-pending and co-assigned U.S. patent application Ser. No. 07/686,049; co-pending and co-assigned U.S. patent application Ser. No. 07/688,138, the disclosures of which are incorporated by reference herein.

When used for diagnostic EKG procedures, electrodes shown in FIGS. 1 and 2 are preferred. When used for monitoring electrocardiogram (ECG) procedures, electrodes disclosed in U.S. Pat. No. 5,012,810 and application Ser. No. 07/686,049 are preferred. When used for defibrillation procedures or electrosurgical procedures, electrodes shown in FIGS. 3 and 4 or disclosed in U.S. Pat. No. 4,539,996 are preferred.

In some instances, the means for electrical communication can be an electrically conductive tab extending from the periphery of the biomedical electrodes such as that seen in U.S. Pat. No. 4,848,353 or can be a conductor member extending through a slit or seam in a insulating backing member, such as that seen in U.S. Pat. No. 5,012,810. Otherwise, the means for electrical communication can be an eyelet or other snap-type connector such as that disclosed in U.S. Pat. No. 4,846,185. Alternatively, an electrically conductive tab such as that seen in U.S. Pat. No. 5,012,810 can have an eyelet or other snap-type connector secured thereto. Further, the means for electrical communication can be a lead wire such as that seen in U.S. Pat. No. 4,771,783. Regardless of the type of means for electrical communication employed, preferably adhesive solid state conductive polymer compositions of the present invention can reside as a field of conductive adhesive on a biomedical electrode for diagnostic, therapeutic, or electrosurgical purposes.

Method of Preparing Solid State Conductive Polymer Compositions

A method of preparing an essentially nonvolatile solid state conductive polymer composition of the present invention can employ a minimum number of ecologically compatible manufacturing steps. The solvating polymer, ionic salt, and essentially non-volatile plasticizer, if any as needed, are mixed into a solvent which is essentially volatile at or above ambient temperatures, such as water, ethanol, methanol, isopropanol, acetone, heptane, and ethyl acetate. A quantity of the mixture of solvating polymer, ionic salt, and any essentially non-volatile plasticizer present in the volatile solvent is then cast onto a surface of a substrate, which can be an inert substrate such as a liner for storage before further processing or a surface of a means for electrical communication having an electrically conductive surface. Then the volatile solvent is essentially evaporated by the application of heat, microwave energy, infrared energy, convective air flow or the like, in order to form the non-volatile solid state conductive polymer composition on the substrate. Typically, a drying oven heated to about 65° C. can be employed. A product liner can optionally be laminated over the field of solid state conductive polymer composition to protect that field from contamination.

An extremely thin coating of solid state conductive polymer composition can be applied to a substrate surface. Coating thickness ranges from about 0.125 mm to about 1.25 mm and preferably from about 0.75 mm to about 1 mm, to yield after evaporation of solvent a coating thickness ranging from about 0.05 mm to about 0.38 mm and preferably from about 0.18 mm to about 0.25 mm. With this extremely thin coating of a conductive, and preferably adhesive, composition on a flexible, electrically conductive substrate, a low profile and conformable biomedical electrode can be made.

Alternatively, solid state conductive polymer compositions of the present invention can be prepared from monomers and crosslinking agents, in a similar process to that described in U.S. Pat. No. 4,524,087 (Engel), the disclosure of which is incorporated herein, using a photoinitiator and a 15 watt blacklight operating about about 350 nm wavelength and 1.2 milliwatts/cm$^2$ intensity for about four minutes in a nitrogen atmosphere. Because no water is required for the resulting solid state conductive polymer composition, no water is added as a part of the process.

Compositions can be prepared in a batch process or in a continuous line process. If prepared by a continuous process, the laminate of a liner, field of non-volatile solid state conductive polymer composition, and substrate can be wound on a roll for bulk packaging and further processing or can be cut using dies known to those skilled in the art into individual electrodes or electrode subassemblies for further processing. U.S. Pat. No. 4,795,516 (Strand) and U.S. Pat. No. 4,798,642 (Craighead et al.), which are incorporated by reference herein, disclose processes and equipment useful for a continuous manufacture of biomedical electrodes involving the dispensing of strips of material from rolls and overlaying such strips in a registered continuous manner in order to prepare a strip of electrodes. Further, co-pending, co-assigned U.S. patent application Ser. Nos. 07/686,049 and 07/688,138 disclose methods of preparing biomedical electrode constructions in a continuous strip subassembly.

For example, one method of continuous strip assembly can be the coating of an aqueous mixture of crosslinked poly(N-vinyl pyrrolidone), polyethylene glycol, and potassium chloride on an electrically conductive surface about 8.9 cm wide, with the coating applied to about the center 5.1 cm section of such width. After evaporation of solvent, the coated electrically conductive surface can be bisected along the strip and also cut orthogonally at about 2.54 cm intervals, yielding a number of electrodes 10 seen in FIG. 1 having dimensions of about 2.54 cm×4.4 cm with a conductive interface portion 18 of 2.54 cm×2.54 cm and a tab portion 20 of 2.54 cm×1.9 cm.

A further description of the invention may be found in the following examples using the following experimental procedures.

EXAMPLES

Example 1

Approximately 100 grams of noncrosslinked poly(N-vinyl pyrrolidone) commercially available from BASF of Parsippany, N.J. in a solid state form of particles having a size from about 10 micrometers to about 75 micrometers were placed in a resealable plastic bag, purged with nitrogen for 15 minutes, irradiated with gamma radiation of 155 kGys using a cobalt-60 high energy source to produce crosslinked solid poly(N-vinyl pyrrolidone).

A mixture was prepared in which 9 grams of crosslinked poly(N-vinyl-2-pyrrolidone) homopolymer was added to a solution consisting of 18 grams of glycerin, 0.1 grams potassium chloride and 90 grams of water. The mixture was stirred until equilibrated, at which time, the mixture was coated onto a 5.1 cm center strip of an 8.9 cm liner silver coated with E1700 silver ink from Ercon, Inc. of Waltham, Mass. The coated strip was dried in an oven at 66° C. for 30 minutes to essentially evaporate the water. A biomedical electrode having the resulting solid state conductive polymer composition on the silver-coated liner was made by cutting an electrode having a conductive portion of 2.54 cm×2.54 cm and a tab portion of 2.54 cm×1.9 cm, tested to determine impedance on a human arm.

Alternating current impedance was measured Measurements were made using an Xtratek ET-65A ECG electrode tester from Xtratek Company of Lenexa, Kans. and conducted in the conventional manner on electrode pairs connected "back-to-back" (adhesive-to-adhesive) using a low level signal suitable for measurements on ECG electrodes. The impedance at 10 Hz was recorded. For skin impedance, twelve panelists were evaluated using biomedical electrodes prepared according to this Example 1 placed on the panelists' arms and measured for alternating current impedance in kOhms at a frequency of 10 Hz using a 4800A Vector Impedance Meter manufactured by Hewlett Packard of Palo Alto Calif. The Association for the Advancement of Medical Instrumentation (AAMI) has adopted acceptable alternating current impedance at a frequency of 10 Hz to be less than 2000 Ohms for "back-to-back" alternating current electrode impedance. Less than about 500 kOhms has been found acceptable for human skin impedance. The performance of the electrodes for skin impedance is listed below in kOhms at time intervals of 0 minutes, 6 minutes and 12 minutes. Table 1 shows the average of the results.

TABLE 1

| Sample | kOhms at $T_0$ min. | kOhms at $T_6$ min. | kOhms at $T_{12}$ min. |
| --- | --- | --- | --- |
| Example 1 | 293 | 211 | 198 |
| Example 2 | 254 | 206 | 201 |

Example 2

A solid state conductive polymer composition was prepared according to Example 1 except that the composition consisted of 9 grams of crosslinked poly(N-vinyl- 2-pyrrolidone), 18 grams of 400 MW polyethylene glycol, and 0.1 grams of potassium chloride. Table 1 shows the results for alternating current impedance for electrodes according to Example 2 on human arms using 16 people using the procedures according to Example 1.

Samples prepared according to Example 2 above were placed in open envelopes to determine shelf life effects on the performance of the electrodes of the present invention. Samples of electrodes were tested at the following time intervals: both at room temperature initially, after 3 days, 1 week, 2 weeks, 4 weeks, and 8 weeks; and at 49° C. after 4 weeks and after 8 weeks. Human skin impedance was measured using a Hewlett-Packard 4800 A Vector Impedance Meter. Direct current offset and back-to-back alternating current impedance were measured using an Xtratek ET-65A ECG electrode tester from Xtratek Company of Lenexa, Kans. Skin adhesion was measured by applying biomedical electrodes on the back of human subjects and rolled with a 2 kg roller to insure uniform application. Electrodes were removed from the back promptly after application using a mechanical pulling device, consisting of a motor driven screw drive which pulls a 11.4 kg test line to which is attached a 2.54 cm wide metal clip. The metal clip is attached to each electrode at its 2.54 cm width during pulling testing. Electrodes were pulled in a plane parallel (180°) to the back at a rate of 13–14 cm/min. The adhesion data is reported in grams/2.54 cm and based on an average of values from initiation of peel to entire removal of the electrode.

The results from this study are shown in Table 2 below. Direct Current Offset was within the AAMI Standard of less than 100 mvolt throughout the test duration. Impedance was within the AAMI standard of less than 2000 Ohms throughout the test duration. Skin impedance at each interval throughout the test duration was less than 500 kOhms.

TABLE 2

| | | CONDUCTIVE POLYMER COMPOSITION ELECTRODES | | | | | |
| --- | --- | --- | --- | --- | --- | --- | --- |
| Time | Aging Temp. | Direct Current Offset (mV) | Impedance (Ohms) | Skin Impedance (kOhms) $t = 0$ min. | Skin Impedance (kOhms) $t = 6$ min. | Skin Impedance (kOhms) $t = 12$ min. | Skin Adhesion (grams) |
| initial | — | 0.9 | 586 | 254 | 206 | 201 | |
| 3 day | RT | 1.8 | 507 | 356 | 303 | 283 | 53 |
| 1 wk | RT | 1.5 | 311 | 313 | 265 | 244 | 64 |
| 2 wk | RT | 1.9 | 414 | 375 | 304 | 285 | 52 |
| 4 wk | RT | 1.2 | 457 | 325 | 249 | 251 | 61 |
| 4 wk | 49° C. | 1.4 | 580 | 370 | 277 | 256 | 137 |
| 8 wk | RT | 0.1 | 404 | 334 | 291 | 262 | 38 |
| 8 wk | 49° C. | 0.3 | 260 | 311 | 232 | 202 | 127 |

Each DC offset and alternating current back-to-back electrode impedance value listed is an average of 16 pairs of electrodes. Skin alternating current impedance and skin adhesion values reported are averages obtained from panels consisting of 24 data points.

Solid state conductive polymer compositions had a DC offset which is below 2 mV consistently throughout the test period of 8 weeks.

Skin adhesion for the electrodes aged at room temperature was quite consistent except for the sample at 8 weeks where there was a decrease in adhesion. Skin adhesion increased upon aging at elevated temperatures. Skin alternating current impedance for electrodes did not change dramatically over the aging period.

Examples 3–7

Skin alternating current impedance and skin adhesion values for solid state conductive polymer compositions were measured for ranges of formulations in which the ratio of solvating polymer: essentially non-volatile plasticizer: ionic salt varied from 46:51:3 weight percent, respectively, to 26:71:3 weight percent, respectively. Each of the formulations were prepared in accordance with Example 2. Crosslinked poly(N-vinyl pyrrolidone) (PVP) prepared according to Example 1 was the solvating polymer. Polyethylene glycol (400 Molecular Weight) was the essentially non-volatile plasticizer. Potassium chloride was the ionic salt. Table 3 reports the results of the average 16 data acquisitions for each of the examples shown in Table 3. The data in Table 3 suggest that a preferred formulation considering both skin impedance and skin adhesion values is about 32 weight percent solvating polymer, 65 weight percent non-volatile plasticizer and about 3 weight percent ionic salt.

TABLE 3

| Example | % PVP | % PEG | % KCl | Skin Impedance (kOhms) t = 0 min. | Skin Impedance (kOhms) t = 6 min. | Skin Impedance (kOhms) t = 12 min. | Alternating Current Impedance (Ohms) | Skin Adhesion (grams) |
|---|---|---|---|---|---|---|---|---|
| 3 | 46 | 51 | 3 | 370 | 308 | 298 | >3000* | 31.3 |
| 4 | 37 | 60 | 3 | 268 | 205 | 201 | 255 | 56.4 |
| 5 | 32 | 65 | 3 | 196 | 215 | 206 | 244 | 67.9 |
| 6 | 29 | 68 | 3 | 177 | 173 | 169 | 246 | 78.8 |
| 7 | 26 | 71 | 3 | 194 | 158 | 155 | 237 | 70.7 |

*Exceeded limit because insufficient adhesion to perform this test between the two electrodes.

Examples 8–14

Electrodes were prepared according to Example 2, except that the amount of the weight percent of ionic salt was varied from about 0.5 weight percent to about 5 weight percent potassium chloride. The remaining 99–95 weight percent, respectively, consisted of a constant ratio of 32 weight percent poly(N-vinyl-2-pyrrolidone) and 65 weight percent polyethylene glycol (400 M.W.).

Skin impedance data was collected in accordance with the procedures of Example 5. Table 4 reports the results.

TABLE 4

| Example | % KCl | Skin Impedance (kOhms) T = 0 min. | Skin Impedance (kOhms) T = 6 min. | Skin Impedance (kOhms) T = 12 min. |
|---|---|---|---|---|
| 8 | 0.5 | 290 | 243 | 235 |
| 9 | 1.0 | 271 | 229 | 217 |
| 10 | 1.5 | 259 | 218 | 208 |
| 11 | 2.0 | 262 | 215 | 203 |
| 12 | 2.5 | 269 | 223 | 212 |
| 13 | 3.0 | 257 | 210 | 201 |
| 14 | 4.0 | 283 | 226 | 296 |

From a comparison of the results of Examples 3–7 with the results of Examples 8–14, the presently preferred formulation of solid state conductive polymer composition of the present invention comprises 33 weight percent crosslinked poly(N-vinyl pyrrolidone), 65 weight percent polyethylene glycol, and 2 weight percent potassium chloride.

Example 15

To 100 gram of water was added 8.9 gram of polyacrylamide (molecular weight, 5 million) commercially available from American Cyanamid of Wayne, N.J. and 2 grams of potassium chloride. The mixture was allowed to swell overnight. Glycerin (89 grams) was added to the swollen mixture and the final mixture was homogenized. The mixture was coated 0.5 mm thick onto a silver conductive backing and dried at 66° C. for 20 minutes. Electrodes were prepared by cutting the material into 2.54 cm×3.81 cm rectangular strip where the top 2.54 cm×2.54 cm area was coated with the mixture, leaving a tab portion of 2.54 cm×1.27 cm of exposed silver conductive backing. A pair of electrodes were connected adhesive to adhesive (back to back) and found to have a D.C. offset value of 0.1 mV and electrode impedance of 100 Ohms. The average skin impedance tested on human arms of 3 volunteers was 189 kOhms.

Example 16

To 3.4 grams of glycerin was added 34 grams of polyacrylamido-2-methyl-propanesulfonic acid, sodium salt, (10% solids in water, commercially available from Aldrich of Milwaukee, Wis.) Potassium chloride (0.2 grams) was then added to the mixture and upon dissolution, the solution was coated at 0.5 mm onto a silver backing and dried in an oven at 66 degrees C. for 15 minutes. Electrodes were prepared according to Example 15. Back-to-back alternating current impedance was determined to be 65 Ohms, DC offset of 9.4 mvolts, and average skin impedance of 275 kOhms averaging results from nine human subjects.

Example 17

To prepare a composition which was cohesive and pliable but not pressure-sensitive adhesive, a mixture was prepared in which 5.5 grams of noncrosslinked poly(N-vinyl-2-pyrrolidone) homopolymer (K-90 commercially available from BASF of Parsippany, N.J.) was added to a solution consisting of 10.8 gram of polyethylene glycol (Pluracol E400, 400 M.W. commercially available from BASF), 15 grams of water and 0.33 grams of potassium chloride. The mixture was stirred until equilibrated. The mixture was then coated at 0.5 mm onto a silver liner and dried for 15 minutes at 66° C. Electrodes were prepared according to Example 15. Alternating current impedance was 1016 Ohms. DC offset was 3.3 mVolt. Average skin impedance was 141 kOhms averaging results from nine subjects.

Example 18

Polyacrylic acid, 10 grams (1,000,000 MW; commercially available from Aldrich), was added to 50 grams of glycerin, 80 grams water and 1.4 grams of potassium chloride. The mixture was stirred and allowed to equilibrate. The mixture was coated onto silver backing at 0.5 mm and then dried at 66° C. for 15 minutes. Electrodes were prepared as described in Example 15. Alternating current impedance was 118 Ohms. DC offset was 0.5 mVolts. An average skin impedance was 164 kOhms using nine subjects.

Example 19

Three samples were prepared with polyacrylic acid, two of which were neutralized with NaOH. The samples were prepared by dissolving 0.25 g of potassium chloride in 30.0 g water followed by the addition of 10.0 g glycerin. Noncrosslinked polyacrylic acid 1.0 g (Aldrich; 1,000,000 MW) was then added to the solution and the resulting mixture was equilibrated for 2 hours. One sample was not neutralized. The second sample was approximately 50% neutralized by the addition of 0.66 g of a 50% by weight aqueous NaOH solution. The third sample was approximately 100% neutralized with the addition of 1.12 g of a 50% by weight aqueous NaOH solution. Electrodes were prepared from these solutions according to the manner described in Example 15. Table 5 shows the results of impedance and voltage measurements.

TABLE 5

| Sample % Neutralized | AC Impedance (Ohms) | D.C. Offset (m volt) |
| --- | --- | --- |
| 0 | 34 | −0.3 |
| 50 | 10 | −0.1 |
| 100 | 31 | −0.4 |

Example 20

To 67.4 grams of glycerin was added 2.5 grams of KCl. The salt solution was mixed in a shaker for 15 hours. In a separate vessel was combined 30 grams of N-vinyl-pyrrolidone, 0.02 grams of diallyl maleate crosslinking agent, and 0.06 grams of 2,2-dimethoxy-2-phenylacetophenone photoinitiator (benzildimethylketal commercially available as "Irgacure 651" from Ciba Geigy). The two mixtures were mixed together and cured under blacklight (350 nm lamp available from Sylvania) operated at a 1.2 milliwatts/cm$^2$ intensity in a nitrogen atmosphere for four minutes in sheet form. Electrodes were constructed by laminating the cured conductive adhesive onto a silver-lined backing, having a conductive portion of 2.54 cm×2.54 cm. The back-to-back impedance was 400 Ohms. The DC offset was 0.8 mV.

Example 21

Electrodes were prepared according to Example 2, except that the plasticizer was polyethylene glycol (300 molecular weight). The electrodes were incubated in humidity chambers at 60% humidity at 37° C. and 90% humidity at 49° C., respectively. The electrodes were weighed before and after the incubation period. Water uptake expressed in percentage water content based on adhesive weight was calculated. The electrical properties of these electrodes were evaluated according to AAMI standards. Results are shown in Table 6.

TABLE 6

| Electrodes | Percent water | DC Offset mV | AC Impedance (Ohms) |
| --- | --- | --- | --- |
| control, no incubation | | 0.1 | 95 |
| 1 | 3 | 2.4 | 66 |
| 2 | 34 | 0.6 | 59 |
| 3 | 48 | 0.4 | 3 |

These results show that solid state conductive polymer compositions of the present invention are ionically-conductive regardless of the amount of water present during storage or use.

Examples 22 and 23

A solution of polyvinylmethylether (50% by weight in water) was obtained from Aldrich Chem. Co. To 16.05 grams of this solution was added 0.4 grams of lithium chloride and 5.6 grams of water. Because the composition was cohesive and pliable, no non-volatile plasticizer was required. The composition was spread onto the silver conductive backing as described in Example 15 and dried to prepare an electrode. The AC impedance of this electrode was determined to be 4 Ohms and a DC offset of 0.0 mV.

Another sample was prepared in which 23 gram of the polyvinylmethyl ether solution was charged with 2 grams of glycerin, 0.53 grams of potassium chloride and 11.08 grams of water. A cohesive and pliable solid state conductive polymer composition formed after drying on a silver coated backing to form an electrode as described in Example 15. The AC impedance was determined to be 2 Ohms and DC offset of 0.0 mV.

Example 24

A copolymer system was prepared consisting of polyacrylamide and poly(vinyl alcohol) (PVA). The PVA was added to increase cohesive properties of the polyacrylamide. A polyacrylamide solution consisted of 10 grams of polyacrylamide, 60 grams of glycerin, 2 grams of KCl and 100 grams of water. A PVA solution was prepared by dissolving 10 grams of PVA (88% hydrolyzed, from Aldrich Chemical) into 70 grams of boiling water with constant stirring, followed by the addition of 20 grams of glycerin. A copolymer mixture was prepared by mixing 10 parts by weight of the polyacrylamide solution to 1 part by weight of the PVA solution. The mixture was coated 0.5 mm thick onto a silver conductive backing and dried at 66° C. for 20 minutes. An electrode was prepared in the manner according to Example 15. The AC impedance was 163 Ohms and DC offset was 0.5 mV.

Example 25

A solid state conductive polymer composition was coated from an aqueous mixture consisting of 25% adhesive solids. A vessel was charged with 11,250 g water and 75.0 g of potassium chloride and then mixed until dissolution. Then 2,437.5 g of PEG 400 (Carbowax brand, Union Carbide) was added and the mixture was stirred until rendered homogeneous. Poly(N-Vinyl-2-pyrrolidone) particles (1,237.5 g of BASF K-90), crosslinked with 155 kGys of gamma radiation in a nitrogen atmosphere) was then added to the mixture and then stirred vigorously for 30 minutes with a high viscosity mixer. The drum was sealed with a plastic bag and then set overnight to equilibrate. After setting for 24 hours the mixture was stirred again and the resultant mixture was ready for coating.

Coating equipment was provided with a knife over bed coater and a drying oven employing 3 total passes, each pass being 3.05 m in length. The three passes were drying passes, each employing a temperature control unit. The adhesive mixture was coated onto a low release polyethylene terephthalate backing (having a Ag/AgCl ink commercially available from Ercon Inc. coated thereon). The adhesive was between 0.8 mm and 1.0 mm thick. Line speed was 1.9 m/min. The temperature of the three drying passes were 121° C., 121° C., and 60° C., respectively.

Glass Transition Temperature Comparison Study

Glass transitions were determined to demonstrate the susceptability of commercially available polyelectrolyte containing biomedical electrodes to dry out as compared with bioelectrodes containing solid state conductive polymer compositions of the present invention. An increase in glass transition temperature indicates a loss of water in the adhesive composition. The glass transition temperatures of a number of commercially available electrodes and electrodes prepared according to these Examples were measured according to the following procedure:

Glass Transition Temperature

The glass transition temperatures reported were measured incorporating a Mettler TA3000 System commercially available from Mettler Instrument Corporation of Hightstown, N.J. The system employs a Mettler TC 10 Processor, a Mettler Differential Scanning Calorimeter (DSC) 30 low temperature cell, and a Minnesota Valley Engineering (MVE) liquid nitrogen reservoir. A sample of adhesive was placed into a 40 microliter aluminum crucible (ME-27331 also from Mettler). The crucible was then placed into a Mettler DSC low temperature cell. The low temperature cell was connected to a MVE cryogenics model LAB 50 vessel, which was filled with liquid nitrogen. DSC thermal analysis was then measured from 50° C. to −140° C. at a rate of 10° C./minute. The glass transition was then determined from the DSC thermal analysis and is reported in Table 6 in °C. The values reported are midpoint values obtained from the DSC curve.

Table 7 compares glass transition temperature for commercially available polyelectrolyte biomedical electrodes and biomedical electrodes of the present invention measured initially and after being exposed to atmospheric conditions for 14 days. Glass transition temperatures were also determined for the electrodes dried at 66° C. for 15 minutes simulating the drying conditions of the solid state conductive polymer composition during processing of the composition. In this instance, electrodes from Examples 1, 15, 17, 18, and 21–23 were reheated to the same temperature for the same duration as employed for preparation of such electrodes initially.

Table 8 shows skin impedance on human arms and back-to-back alternating current electrode impedance.

TABLE 7

| Conductive Adhesive Composition | Tg, initial | Tg, aging 2 weeks | Tg, drying 65° C., 15 min |
|---|---|---|---|
| Q-Trace ™ Electrode[1] | −98.5* | −68.5 | −70.4 |
| Fastrace 4 ™ Electrode[2] | −88.4* | −70.7 | −74.9 |
| Tracets AG 4000 ™ Electrode[3] | −84.5* | −70.7 | −75.7 |
| Tracets MP 3000 ™ Electrode[3] | −84.2* | −70.3 | −73.7 |
| Signal ™ Electrode[4] | −96.9* | −76.7 | −80.1 |
| Example 1 | −83.2 | — | −81.3 |
| Example 15 | −86.4 | — | −82.3 |
| Example 17 | −66.5 | — | −65.8 |
| Example 18 | −86.2 | — | −80.6 |
| Example 21 | −71.1 | −72.9 | −68.3 |
| Example 22 | −31.8 | — | −28.0 |
| Example 23 | −32.9 | — | −29.9 |

[1]Commercially available from Graphic Controls, Medi–trace Products Div., Buffalo N.Y.
[2]Commercially available from Medtronic Andover Medical, Haverhill, Massachusetts
[3]Commercially available from Lectec Corporation, Minnetonka, Minnesota
[4]Commercially available from Minnesota Mining and Manufacturing Company, St. Paul, Minnesota
*Initial testing promptly after removal from protective packaging The changes in glass transition temperatures of the electrode samples commercially available demonstrate a sensitivity of these systems to a loss of water. By contrast, the glass transition temperature of each polymer electrolyte electrode containing a solid state conductive polymer composition of the present invention did not change essentially after 14 days or after a second heating at 65° C. for 15 minutes, because the solid state conductive polymer composition of the present invention did not contain water or other volatile plasticizers susceptible to evaporation. Thus, ionic conductivity of solid state conductive polymer compositions of the present invention are retained after exposure to atmospheric conditions.

The present invention is not limited to the above embodiments. For an appreciation of the scope of the present invention, the claims follow.

What is claimed is:

1. A solid state conductive polymer composition comprising:

(a) an ionically conductive polymer electrolyte complex formed by a process where the complex is effectively dehydrated by essentially evaporating water, and (b) optionally if the complex is not cohesive and pliable, an essentially non-volatile plasticizer present in an amount of from about 0 to about 95 weight percent of the composition;

said polymer electrolyte complex comprising a solid solution of an ionic salt dissolved in a solvating polymer wherein the complex is ionically conductive after processing;

said solvating polymer present in an amount of from about 5 to about 98 weight percent of the composition;

said ionic salt present in an amount of from about 0.5 to about 5 weight percent of the composition;

said solvating polymer comprising polyacrylamide and its ionic forms; polyacrylic acid and its salts; poly(vinyl alcohol); poly (vinyl methyl ether); poly(2-acrylamido-2-methylpropane sulfonic acid), its salts, copolymers of the acid, copolymers of salts of the acids, or mixtures thereof, or combinations thereof;

wherein the composition maintains its glass transition properties and maintains its alternating current impedance properties below 2000 Ohms notwithstanding exposure to ambient air conditions for at least two weeks.

2. The composition according to claim 1, further comprising an iontophoretically active pharmaceutical associated with the composition.

TABLE 8

| Electrodes | DC offset mV | | AC Impedance, Ohms | | Skin Impedance, kOhms | |
|---|---|---|---|---|---|---|
| | T, initial | T, 2W | T, initial | T, 2W | T, initial | T, 2W |
| Example 21 | 1.0 | 3.3 | 143 | 255 | 153 | 230 |
| Signal ™ Electrode | 0.1 | 0.4 | 149 | 674 | 135 | 553 |
| Tracet Ag 4000 ™ Electrode | 0.0 | 0.6 | 940 | 3700 | 364 | 860 |
| Tracet MP 3000 ™ Electrode | 0.2 | 1.1 | 68 | 1186 | 277 | 677 |
| Fastrace 4 ™ Electrode | 0.1 | 0.1 | 623 | 935 | 216 | 456 |
| Q-Trace ™ Electrode | 2.1 | 0.1 | 467 | 878 | 140 | 650 |

3. The composition according to claim 1, wherein said solvating polymer comprises crosslinked polyacrylamide and its ionic forms; crosslinked polyacrylic acid and its salts; crosslinked poly(2-acrylamide- 2-methylpropane sulfonic acid), its salts, crosslinked copolymers of the acid, crosslinked copolymers of salts of the acid, or mixtures thereof; or combinations thereof; and wherein the plasticizer is present in an amount of from about 65 to about 95 weight percent of the composition to form a cohesive, pliable and pressure-sensitive adhesive composition.

4. The composition according to claim 1, wherein said ionic salt comprises lithium chloride, lithium perchlorate, sodium citrate, potassium chloride, or mixtures thereof.

5. The composition according to claim 4, wherein said ionic salt is potassium chloride present in an amount of from about 2 to about 3 weight percent of the composition.

6. The composition according to claim 1, wherein said plasticizer is a polyhydric alcohol comprising glycerin, polyethylene glycol, or mixtures thereof.

7. The composition according to claim 5, wherein said plasticizer is polyethylene glycol present in an amount of about 65 weight percent of the composition.

* * * * *